United States Patent [19]
Tobia et al.

[11] Patent Number: 5,265,639
[45] Date of Patent: Nov. 30, 1993

[54] MAGNETO-PNEUMATIC TIMING DEVICE

[75] Inventors: Ronald L. Tobia, Tinton Falls; Russell J. Fischer, North Plainfield, both of N.J.

[73] Assignee: BOC Health Care, Inc., Liberty Corner, N.J.

[21] Appl. No.: 995,610

[22] Filed: Dec. 22, 1992

[51] Int. Cl.⁵ ............................................ G05D 16/06
[52] U.S. Cl. .................... 137/103; 137/624.14; 251/65
[58] Field of Search .................. 137/103, 105, 624.14; 251/65; 604/120

[56] References Cited

U.S. PATENT DOCUMENTS

| | | |
|---|---|---|
| 2,292,401 | 8/1942 | Orre ..................... 137/103 |
| 2,652,847 | 9/1953 | Segebarth .................. 137/103 |
| 2,669,249 | 2/1954 | Wittmann .................. 251/65 X |
| 2,991,805 | 7/1961 | Page ..................... 251/65 X |
| 3,216,328 | 11/1965 | Peterson .................. 137/624.14 |
| 3,659,605 | 5/1972 | Sielaff . |
| 3,812,855 | 5/1974 | Banko . |
| 4,303,072 | 12/1981 | Lewis . |
| 4,315,506 | 2/1982 | Kayser et al. . |
| 4,600,034 | 7/1986 | Ko . |
| 4,635,681 | 1/1987 | Boldish . |
| 4,747,577 | 5/1988 | Dimock . |
| 4,750,705 | 6/1988 | Zippe . |
| 4,767,403 | 8/1988 | Hodge . |
| 4,782,849 | 11/1988 | Hodge .................. 137/103 |
| 4,782,849 | 11/1988 | Hodge . . |
| 4,819,693 | 4/1989 | Rodder . |

FOREIGN PATENT DOCUMENTS

970912 9/1964 United Kingdom .

*Primary Examiner*—Robert G. Nilson
*Attorney, Agent, or Firm*—Roger M. Rathbun; Larry R. Cassett

[57] ABSTRACT

A magneto-pneumatic timing device is disclosed that provides a pressure signal alternating between a high and a low pressure output signal. The duty cycle may be varied as well as the overall cycle time. A magnetically biased flexible diaphragm divides a chamber into a pair of subchambers and the differential pressure between the subchambers is controlled to cause the flexible diaphragm to pull away from the magnetic bias to one position and to return to its biased position. Control of the output pressure signal is carried out by varying the resistance in certain of the pneumatic passages that are part of the control function for the differential pressure. The device is relatively simple and inexpensive to construct and features very few moving parts, thus it is reliable and capable of high production, low cost manufacture.

18 Claims, 4 Drawing Sheets

MAGNETO-PNEUMATIC TIMING DEVICE

BACKGROUND OF THE INVENTION

This invention relates to a timing device and, more particularly, to a magneto-pneumatic timing device that may be used to provide a timed pressure signal for an end use and which has few moving parts and yet which has a output signal waveform that is easily modified in shape and in timing cycle.

Pneumatic timing devices are currently used for various purposes and are intended to provide a timed output pressure signal where that signal cycles between a higher and a lower value. The timing ratio between the signals, that is, the duty cycle as well as the overall time cycle may vary depending upon the particular application of or use for that signal. In any event, the timed output pressure signal can thus be used to control some end use device. An example of such an end use device is an intermittent suction device used in the withdrawal of fluid from a medical patient and is described in copending patent application by the same assignee as the present application and entitled "Magneto-Pneumatic Intermittent Suction Device", Ser. No. 995,391, filed Dec. 22, 1992 the disclosure of which is made part of the present application.

One of the features desired in such timing devices is that the device be reliable and be capable of functioning without supervision or maintenance for long periods of time and, accordingly, it is desired that the device have a minimum of moving parts that could wear out. The device should also be easy and inexpensive to manufacture. The latter feature requires that the components be relatively inexpensive and the assembly be simple and free of complex steps and extremely close tolerances.

BRIEF SUMMARY OF THE INVENTION

The present magneto-pneumatic timing device thus is powered by a differential pressure and therefore the energy required to operate the device is readily available in many locations. In the intermittent suction device of the corresponding aforementioned patent application, the differential pressure is provided by a vacuum source and a source of atmospheric pressure. Those sources are, of course, convenient for the end use of the device since both of those sources are available in the normal hospital environment. Alternately, the differential pressure to power the present device could be provided by means of a positive pressure and atmospheric pressure.

In any case, depending on the end use of the timing device, a source of a differential pressure is generally accessible.

The present device is also comprised of an extremely few moving parts and thus is not susceptible to wear. Assembly is relatively easy and can be accomplished without detailed or complex operations, thus overall assembly is fairly inexpensive.

As a further feature of the present magneto-pneumatic timing device, the overall time cycle can easily be varied in accordance with the requirements of the end use device and, within that overall time cycle, the duty cycle is also readily adjustable.

Thus, the magneto-pneumatic timing device of the present invention is versatile and can be used for a variety of duty cycles and is easily adapted to such duty cycles and modified as needed.

BRIEF DESCRIPTION OF THE DRAWINGS

The above and other features and embodiments of this invention will become still further apparent from a consideration of the following description and accompanying drawings which show the preferred embodiment of the invention in which.

DESCRIPTION OF THE PREFERRED EMBODIMENT

Figure 1:
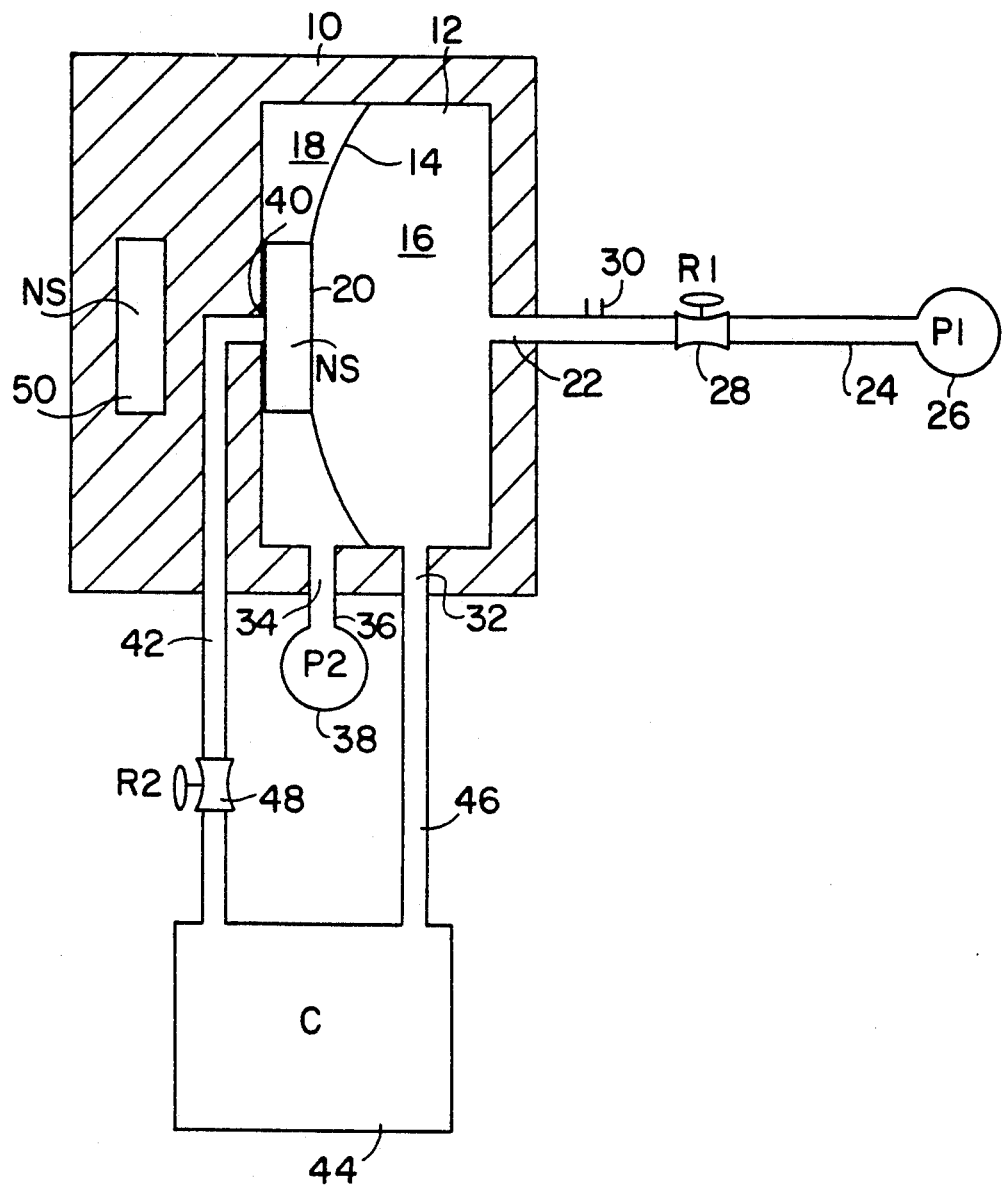
FIG. 1 is a schematic view of the present invention in its position at start-up and when the higher pressure signal is being communicated at the outlet port.

Referring now to FIG. 1, there is shown a schematic view of a magneto-pneumatic timing device constructed in accordance with the present invention. A housing 10 is provided and within which there is formed a chamber 12. A flexible diaphragm 14 is sealed, within the interior of chamber 12 and separates the chamber 12 into first and second subchambers 16,18 respectively.

Flexible 14 diaphragm is manufactured such that it is susceptible to magnetic forces and thus is attracted and/or repelled by a magnetic force. In the embodiment shown, a permanent magnet 20 is affixed to a non-magnetic diaphragm, or, as an alternate, the flexible diaphragm 14 itself could be manufactured by using a magnetically polarized diaphragm material. In either case, or in the case of some alternate, the important property required in the diaphragm is that it be magnetically susceptible to magnetic forces having a polarity, that is, a north and south magnetic orientation.

A first port 22 is formed in first subchamber 16 of chamber 16 and is connectible, by means such as a tubing 24, to a first source of a known pressure 26. The first pressure source 26 will be later explained, however it should be noted that the first pressure source 26 may be the source of a negative pressure, such as a vacuum as described in the copending above-referred to application.

A variable restrictor 28 is also located in the tubing 24 intermediate the source of pressure 26 and the first port 22. As will become clear, the variable restrictor 28 may be adjusted, by hand or some automated means, to vary the pneumatic resistance in the tubing 24. Although a variable restrictor is disclosed as the preferred embodiment, obviously, if the duty cycle is fixed, the restrictor need not be variable but may be fixed with the specific resistance needed to achieve the desired duty cycle. A signal outlet port 30 is formed in tubing 24 and is located intermediate variable restrictor 28 and first port 22 and which provides the output signal from the timing device as will be explained.

A bypass port 32 is formed in the first subchamber 16 of the chamber 12 and its purpose also will be explained later.

In the second subchamber 18 of chamber 12, there is formed a port 34 and which leads via suitable tubing 36 to a second source of pressure 38. Again, the actual pressure used as the second source may vary according to the end use of the present timing device, however it is important to note that the second pressure source 38 is at a higher pressure than the first source of pressure 26.

A further bypass Port 40 is formed in housing 10 and which communicates with the second subchamber 18 of chamber 12. A bypass path is thus formed that creates a path of communication between the first subchamber 16 and the second subchamber 18 between the two bypass ports 32 and 40. That bypass path is provided by a tubing 42 from bypass port 40 through a compliance chamber 44 and thus with bypass port 32 by tubing 46. It should be noted that the means of communication are referred to as tubings, however any conduit would be suitable, and including passages formed into the housing 10. Such passages could readily be formed in an injection molded housing 10 during the molding process.

A variable restrictor 48 is located in the bypass path communicating between the first and second subchambers 16, 18 and is located intermediate the compliance chamber 44 and bypass port 40 along tubing 42. Again, if a nonadjustable duty cycle is usable, the variable restrictor 48 may be a fixed restrictor having the resistance needed for the specified set duty cycle. As will also become apparent, the compliance chamber 44 may have its volume varied to change the timing cycle either in conjunction with or independent of a change in the resistance in the bypass path by changing the variable restrictor 48.

A permanent magnet 50 is positioned within housing 10 sufficiently close to the flexible diaphragm 14 so as to create a magnetic attraction or bias on diaphragm 14. Obviously, the polarity is such that the permanent magnet 50 has an opposite pole facing the pole of the diaphragm permanent magnet 20 such that the flexible diaphragm 14 is biased to its first position as shown in FIG. 1.

Figure 2:
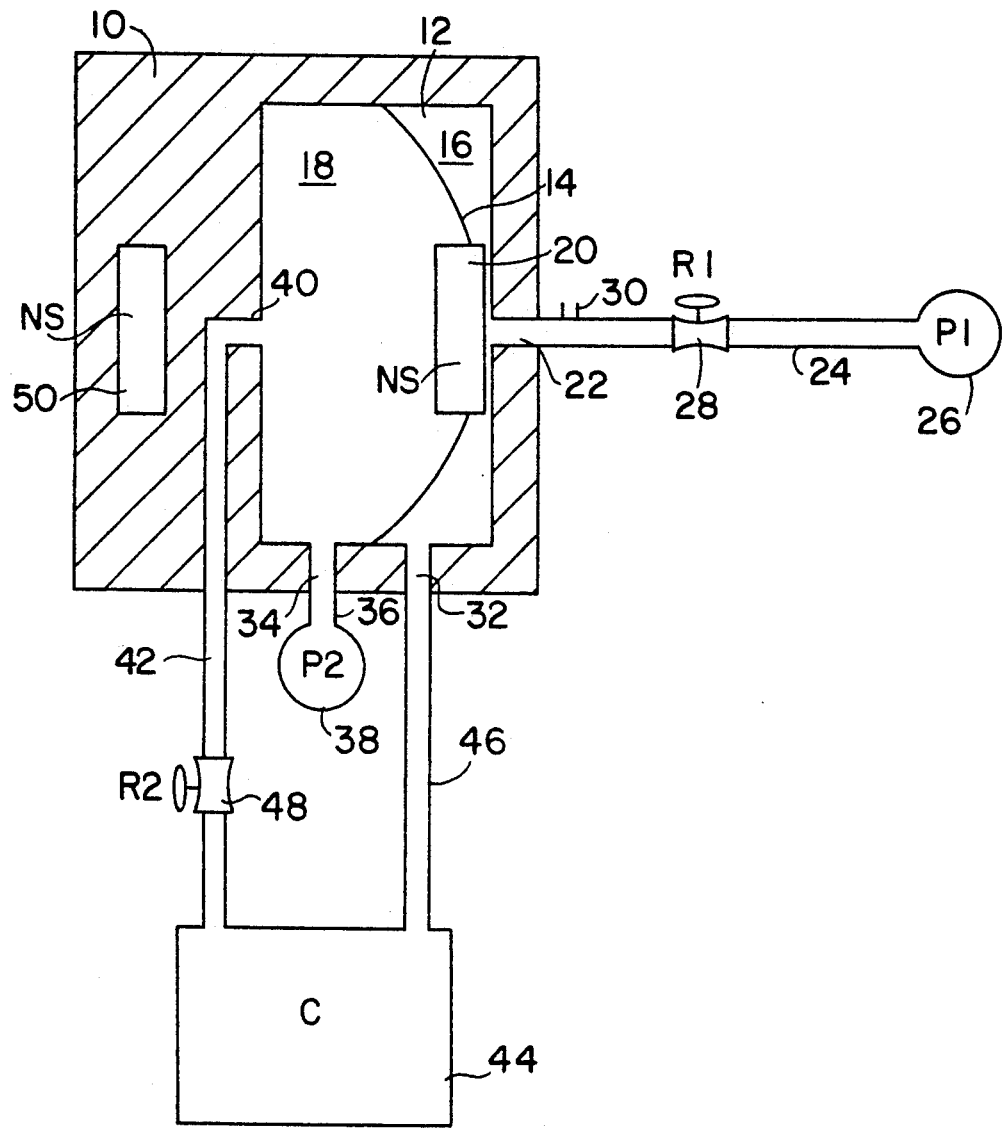
FIG. 2 is a schematic view of the present invention where the lower pressure signal is being communicated.

Having described the overall structure of the magneto-pneumatic timing device of the present invention, a summary of its operation will now be presented with reference to both FIG. 1 where flexible diaphragm 14 is in its first position and FIG. 2 wherein flexible diaphragm 14 is shown in its second position.

Initially the timing device is as shown in FIG. I prior to initiation of the cycle. As explained, the magnetic bias exerted by the permanent magnet 50 on the magnetic force susceptible flexible diaphragm 14 retains that diaphragm 14 in its first position as shown in FIG. 1. In the embodiment where the first pressure source 26 is a negative pressure or vacuum, that vacuum is applied to the compliance chamber 44 through variable restrictor 28 through open port 22. The pressure in the compliance chamber 44 thus begins to decrease at a rate that is determined by the value of the resistance set at variable restrictor 28 and by the capacity of volume of compliance chamber 44.

Eventually, the pressure drops sufficiently within the first subchamber 16 of chamber 12 to create a sufficient pressure differential between the first subchamber 16 and the second subchamber 18, which is at the pressure of the second pressure source 38 and which has been explained to be more positive than the pressure of first pressure source 26. That differential pressure eventually becomes sufficient to overcome the magnetic bias exerted on the flexible diaphragm 14 by permanent magnet 50 and the flexible diaphragm 14 moves from its first position as shown in FIG. 1 to its second position as shown in FIG. 2 where it seals against port 22, thereby closing off the source of pressure of the first pressure source 26 to the first subchamber 16 of chamber 12.

Since the port 22 is now closed, the pressure signal at the outlet signal port 30 rapidly drops to the pressure at the first pressure source 26. thus establishing the lower of the two pressure signals available from the timing device.

At this point (FIG. 2). the compliance chamber 44 is in communication with the second source of pressure 38 through port 40 and variable restrictor 42. The pressure within compliance chamber 44 therefore increases at a rate determined as a function of the resistance set at variable restrictor 48 and the capacity or volume of compliance chamber 44. The variable restrictor 48 is, of course, adjustable to set the rate at which the pressure within compliance chamber 44 increases.

Eventually, the pressure within compliance chamber 44 has increased such that the differential pressure across flexible diaphragm 14 is reduced to a threshold value where it is no longer sufficient to counteract the magnetic bias exerted on flexible diaphragm 14 by permanent magnetic 50 causing flexible diaphragm 14 to move back to its first position as shown in FIG. 1. At this occurrence, the output pressure signal at pressure signal port 30 changes to the higher of the two output pressure signals.

As the cycle continues, the first pressure source 26 again commences to lower the pressure within the compliance chamber 44 and first subchamber 16 to again create sufficient differential pressure between subchambers 18 and 16 to overcome the magnetic bias exerted on flexible diaphragm 14 by permanent magnet 50 to move the flexible diaphragm to its second position. The timing of that movement is again controlled by the volume of the compliance chamber 44 and the resistance set at variable restrictor 28.

Figure 3:
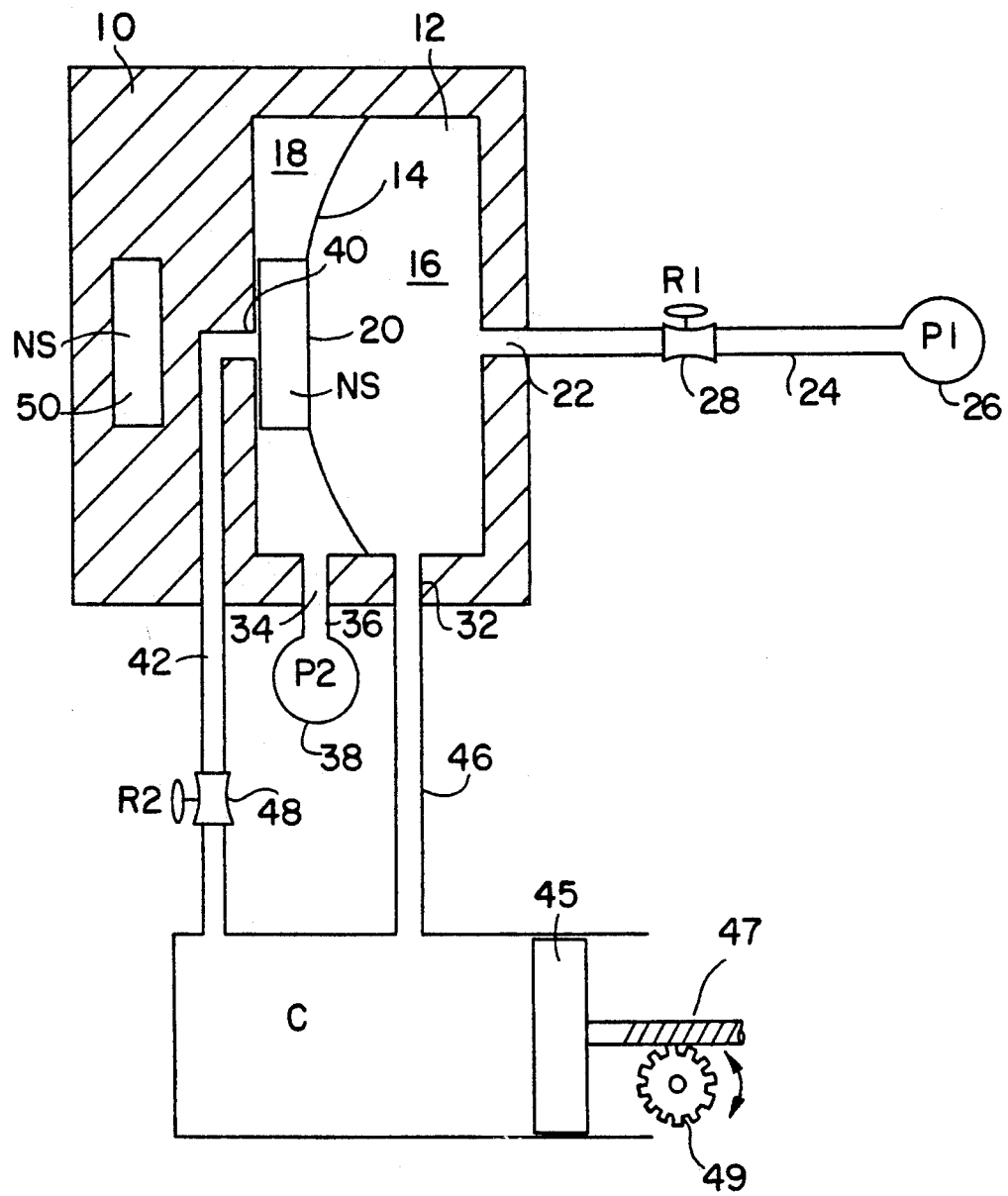
FIG. 3 is a schematic view of the present invention having a variable compliance chamber.

As can thus be seen, the output signal port 30 provides a pressure signal that alternates between two defined pressures and which can therefore be used to operate an end use device. The overall time for the device to carry out one complete duty cycle, that is a cycle where both pressures are present, can be modified by changing the volume of the compliance chamber 44. As an example, the compliance chamber may be fixed in accordance with the particular end use device, or can be a variable volume such as with a movable piston, so that the overall cycle time of any device may be easily changed manually by an operator or by some other signal. An example of a variable volume compliance chamber 44 is shown in schematic in FIG. 3 where a piston 45 controls and can change the internal volume of the compliance chamber. One of the many means that can be used to move the piston 45 is shown including a threaded piston shaft 47 actuated by a gear 49 which may be manually operated or via some automatic means.

The timing ratio, or duty cycle, of the individual high and low pressure signals can be individually adjusted by changing the resistances set by variable restrictors 28 and 48. The variable restrictor 28 sets the timing of the high pressure portion of the duty cycle while the variable restrictor 48 sets the time of the lower pressure portion.

Figure 4A:
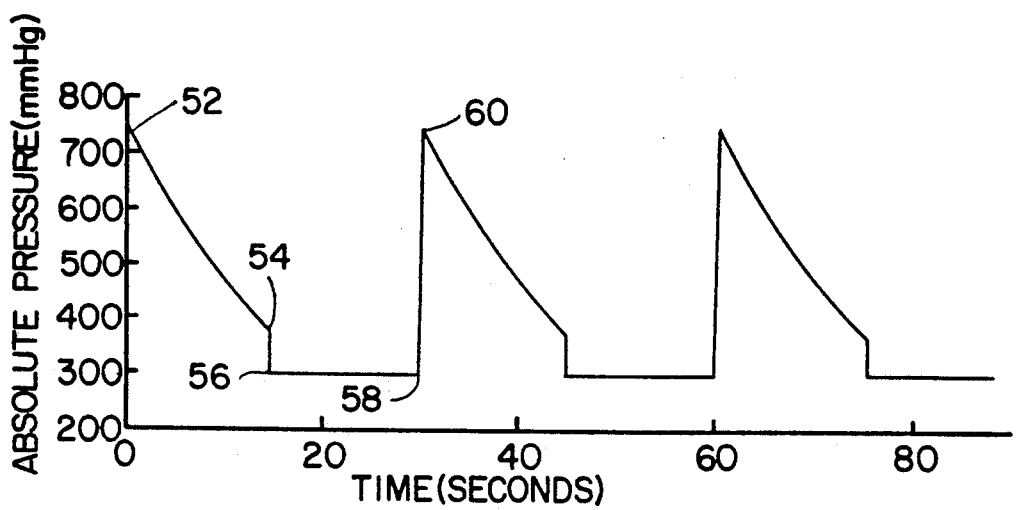
FIGS. 4A, 4B and 4C are representative waveforms that may be communicated from the present timing device to an end use device.
Figure 4B:
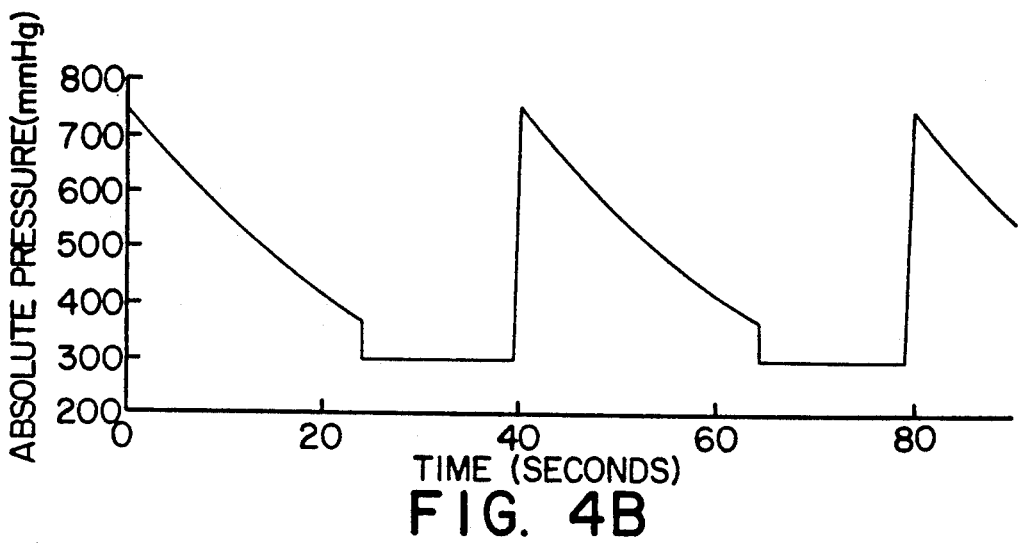
Figure 4C:
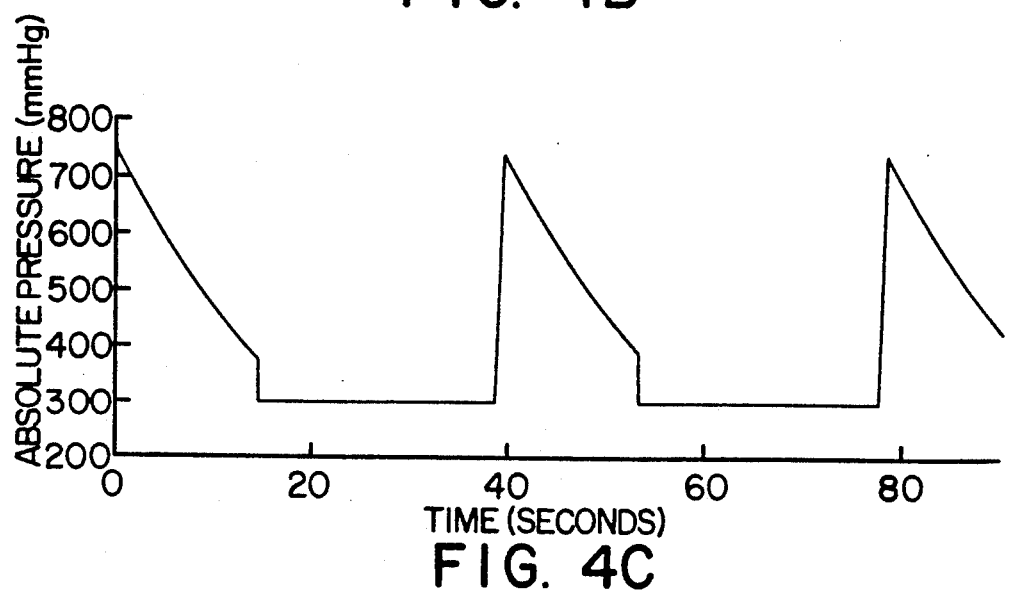

Turning now to FIGS. 4A-4C, there are shown a series of representative curves showing the pressure signal that is present at output signal port 30 as the magneto-pneumatic timing device is cycled. The X axis of the curves is in absolute pressure (mmHg) while the Y axis is in seconds. Again, the curves represent the embodiment wherein the first pressure source is a vacuum and the second pressure source is at atmospheric pressure. It should be noted that the high pressure output signal is normally somewhat lower than the actual pressure of the high pressure source itself.

Taking first, the curve of FIG. 4A, the cycle shown commences at point 52 where the output signal port 30 communicates atmospheric pressure. As the first pressure source 26 draws down the pressure, the pressure at port 30 is reduced at a rate established by the setting of variable restrictor 28 and the volume of the compliance chamber 44. Eventually, as explained, the differential pressure across flexible diaphragm 14 reaches the point where it moves that flexible diaphragm 14 to its position as shown in FIG. 2. This occurs at point 54 on the curve of FIG. 4A and the pressure signal at output signal port 30 immediately drops to the pressure of the first pressure source 26 at point 56 (in the embodiment shown, vacuum of about 300 mm.Hg.). The output lower pressure signal will continue at signal pressure port 30 until, as explained, the differential pressure across the flexible diaphragm 14 is reduced to the point that the magnetic bias exerted on the magnetically susceptible diaphragm causes the flexible diaphragm 14 to move again to its first position, shown in FIG. I and the pressure at the output signal port 30 changes rapidly from the lower pressure value, at 58, to return to the higher pressure value at 60. In the curve of FIG. 4A, the cycle thus continues and, as shown, the magneto-pneumatic timer device cycles between the higher and lower pressures at interval of about 15 seconds for each portion of the cycle, the complete cycle represented by that portion of the curve between point 52 and 60.

Turning now to the curve of FIG. 4B. the points of the curve are labeled with consistent numbers to show the points as described with respect to FIG. 4A. In FIG. 4B, however, the length of the higher pressure signal value has been extended to about 22 seconds by closing, to some extent, the variable restrictor 28. Thus the time for that portion of the overall cycle is easily modified as well as the length of the overall cycle time(- now extended to about 40 seconds).

Finally, in the curve of FIG. 4C, the time of the cycle when the output pressure signal is at its lower value has been extended by closing, to some degree, the variable restrictor 48. In that case, the lower value pressure signal is present at output signal port 30 for about 22 seconds.

As can be seen, therefore, by a simple adjustment of the variable restrictors 28 and 48, the output waveform of the pressure signal at output signal port 30 can be easily modified and the timing cycle set to a wide range of values and times necessary for the particular end user of that signal. The overall device is, however, still fairly simple and reliable in its design and use.

We claim:

1. A magneto-pneumatic timing device operable from a source of differential pressure provided by a first pressure source and a second pressure source at a higher pressure than the first pressure source to provide an output pressure signal to an end use device alternating between high and a low output pressures at a predetermined duty cycle, said timing device comprising:
    a housing, said housing having a chamber having a flexible diaphragm separating said chamber into first and second subchambers, said device having an inlet communicating with said first subchamber, conduit means connecting said inlet to said first pressure source, said conduit having an outlet intermediate said inlet and said first pressure source for connection to the end use device, said flexible diaphragm having a first position wherein said high output pressure is provided at said outlet and a second position wherein said low output pressure is provided at said outlet, said diaphragm being susceptible to magnetic forces, magnetic force means biasing said diaphragm to said first position, and means to control the differential pressure between said first and said second subchambers to move said flexible diaphragm between said first and said second positions.

2. A magneto-pneumatic timing device as defined in claim 1 wherein said magnetic force means is a permanent magnet.

3. A magneto-pneumatic timing device as defined in claim 1 wherein said first subchamber includes a bypass port and said second subchamber includes a bypass port and said means to control the differential pressures includes a bypass flowpath connecting said bypass ports of said first and said second subchamber.

4. A magneto-pneumatic timing device as defined in claim 3 wherein said bypass flowpath includes a restrictor and a compliance chamber.

5. A magneto-pneumatic timing device as defined in claim 4 wherein said flexible diaphragm closes said inlet when said flexible diaphragm is in said second position and said low pressure output signal is communicated from said first pressure source through said conduit to said outlet.

6. A magneto-pneumatic timing device as defined in claim 4 wherein said flexible diaphragm closes said bypass port in said second subchamber when said flexible diaphragm is in its first position and said high pressure output signal is communicated from said bypass flowpath through said first subchamber to said outlet.

7. A magneto-pneumatic timing device as defined in claim 4 wherein said conduit includes a restrictor intermediate said outlet and the first pressure source.

8. A magneto-pneumatic timing device as defined in claim 7 wherein said restrictor in said conduit is a variable restrictor.

9. A magneto-pneumatic timing device as defined in claim 4 wherein said restrictor in said bypass flowpath is a variable restrictor.

10. A magneto-pneumatic timing device as defined in claim 4 wherein said compliance chamber is a variable volume compliance chamber.

11. A magneto-pneumatic timing device as defined in claim 8 wherein said bypass flowpath communicates between said first and second subchambers when said flexible diaphragm is in its second position to allow a timed reduction of the differential pressures between said first and second subchamber to a threshold level whereby said magnetic bias force causes said flexible diaphragm to move to its first position.

12. A magneto-pneumatic timing device as defined in claim 11 wherein the timed reduction of differential pressures is controlled by said variable restrictor in said bypass flowpath.

13. A magneto-pneumatic timing device operable from a source of differential pressure provided by a first pressure source and a second pressure source at a higher positive pressure than the first pressure source to provide an output pressure signal alternating between a high and a low output pressure at a timed interval, said timing device comprising:

a housing having a chamber formed therein, said chamber having a magnetically attractable flexible diaphragm separating said chamber into a first and a second subchamber, said first subchamber having an inlet, a conduit means connecting said first subchamber inlet to the first pressure source, said conduit having a restrictor located intermediate the first source of pressure and said inlet, said first subchamber further having a bypass port, said second subchamber having a inlet, a conduit means connecting said second subchamber inlet to the second pressure source, said second subchamber further having a bypass port, a bypass path communicating between said bypass port of said first subchamber and said bypass port of said second subchamber, said bypass path having a restrictor and a compliance chamber therein, said diaphragm having a first position where said bypass port of said second subchamber is closed and the high outlet pressure signal is communicated to said outlet and a second position where said inlet of said first subchamber is closed and the low output pressure signal is communicated to said outlet, a permanent magnet secured to said housing and magnetically biasing said diaphragm to its first position, and control means to control the differential pressure between said first and said second subchamber, said control means increasing the differential pressure between the first and second subchambers over a predetermined time to overcome the magnetic bias to move said diaphragm from its first position to its second position, said control means further decreasing said differential pressure over a predetermined time to cause said magnetic bias to move said diaphragm from said second position to said first position.

14. A magneto-pneumatic timing device as defined in claim 13 wherein said restrictor in said bypass path is a variable restrictor.

15. A magneto-pneumatic timing device as defined in claim 13 wherein said compliance volume in said bypass path is a variable volume compliance chamber.

16. A magneto-pneumatic timing device as defined in claim 14 wherein said restrictor in said conduit is a variable restrictor.

17. A magneto-pneumatic timing device as defined in claim 16 wherein said variable restrictors in said conduit and said bypass path control the duty cycle of said device.

18. A magneto-pneumatic timing device as defined in claim 17 wherein said flexible diaphragm has a permanent magnet affixed thereto.

* * * * *